United States Patent [19]
Kerr et al.

[11] Patent Number: 4,975,682
[45] Date of Patent: Dec. 4, 1990

[54] MEAL MINDER DEVICE

[76] Inventors: Glenn E. Kerr, 915 8th Ave. NE.;
Larry L. Rott, 1700 11th Ave. NE.,
both of Jamestown, N. Dak. 58401

[21] Appl. No.: 215,793

[22] Filed: Jul. 5, 1988

[51] Int. Cl.$^5$ ............................................. G08B 21/00
[52] U.S. Cl. .................................. 340/573; 340/309.4;
340/540; 340/568
[58] Field of Search ................... 340/573, 540, 309.15,
340/309.4, 568

[56] References Cited

U.S. PATENT DOCUMENTS

| | | | |
|---|---|---|---|
| 3,934,240 | 1/1976 | Norling | 340/309.15 |
| 4,012,732 | 3/1977 | Herrick | 340/573 |
| 4,275,384 | 6/1981 | Hicks et al. | 340/309.15 |
| 4,801,921 | 1/1989 | Zigenfus | 340/573 |

*Primary Examiner*—Glen R. Swann, III
*Attorney, Agent, or Firm*—Robert E. Kleve

[57] ABSTRACT

The invention comprises a signalling device for reminding a person to follow certain eating habits. The device acts to sound an alarm at certain timed intervals in conjunction with the placement of a utensil upon the device to indicate to the person when he is eating too fast or without suitable interruption. The device has a photo cell at a convenient location on top of the device to receive the utensil so that the utensil will block out the light and cause the photo cell to react, in turn causing the circuitry of the device to react. If the operator removes the utensil from the photo cell for each bite and replaces it at that location, the device acts to regulate the amount of time the operator has the utensil away from the photocell presumably to take a bite and regulate the amount of time the utensil must be left on the photo cell between each bite. The operator must replace the utensil over the photo cell within a specified period of time, timed by the device, after removing it presumably to take a bite, or the alarm will sound when that specified time has elapsed, which period of time is considered adequate for taking a bite of food. The operator, once he has replaced the utensil over the photo cell, must leave it at this location for a specified period of time, as timed and programmed by the device, before he can remove it again to presumably take another bite, or the device will also cause the alarm to sound if he removes it before that time has elapsed, indicating to the operator he has removed the utensil from the photo cell too soon for another bite, in the time estimation as programmed or timed by the device.

4 Claims, 1 Drawing Sheet

U.S. Patent     Dec. 4, 1990     4,975,682
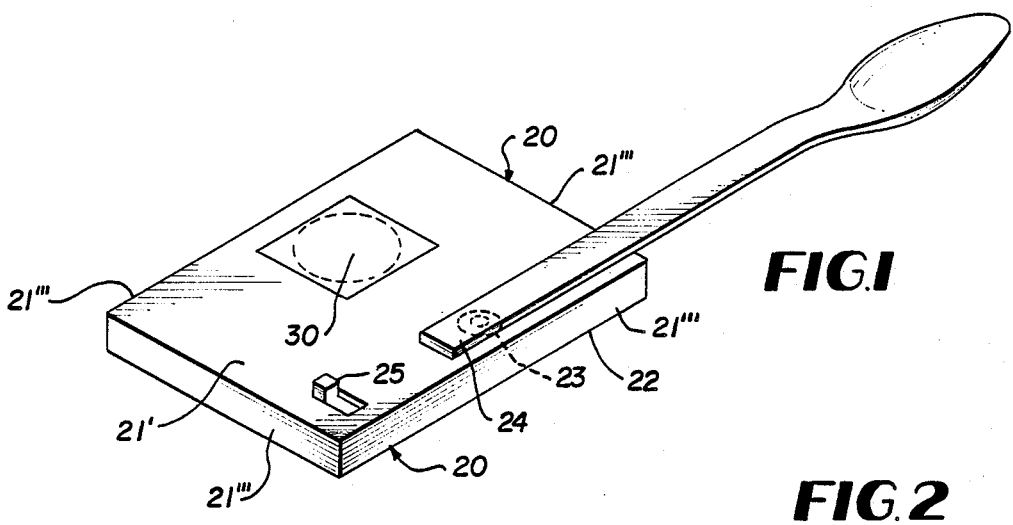
FIG.1
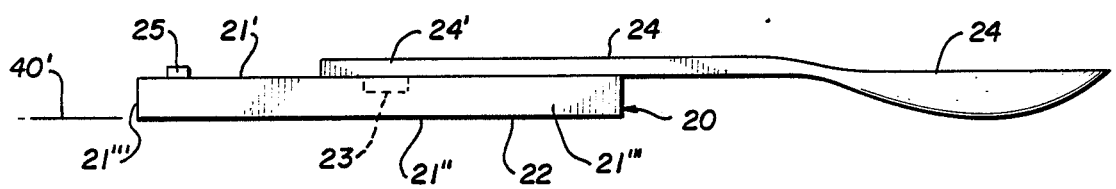
FIG.2
FIG.3
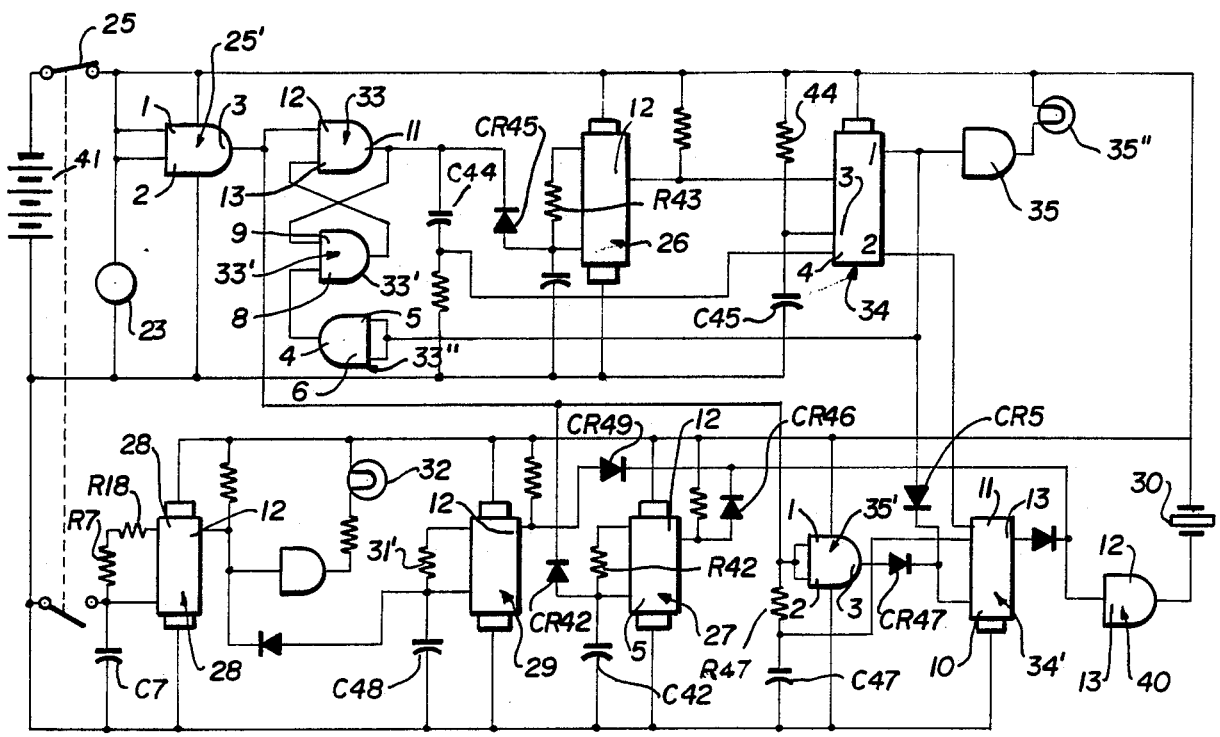

MEAL MINDER DEVICE

BACKGROUND OF THE INVENTION

This invention relates to signalling devices for maintaining and training persons concerning their eating habits so as to maintain a certain pace when eating.

It is an object of the invention to provide a novel invention to signal to a person when the person is eating at too rapid a pace or speed.

It is a further object of the invention to provide a novel signalling device which will sound an alarm if an operator, when using a utensil for eating, does not replace the utensil at a specified place within a specified time to prevent the operator from using the utensil too long to prevent eating too long.

It is a further object of the invention to provide a novel signalling device which will sound an alarm if the operator, using a utensil for eating, places it upon the invention within a specified time at a specified location presumably after taking a bit of food but removes the utensil from that location before a specified period of time determined by the device has elapsed before presumably taking another bite.

It is a another object to provide a novel device that assists a person to establish a rate of eating for that person that would result in meals being eaten and completed without triggering the alarm in the device if the person followed that rate of eating.

It is another object of the invention that acts to limit the amount of food intake by limiting the amount of time allowed for eating.

BRIEF DESCRIPTION OF THE DRAWING

Further objects and advantages of the invention will become apparent as the description proceeds and when taken in conjunction with the accompanying drawing wherein:

FIG. 1 is a perspective view of the signalling device with a metal utensil placed over the photocell of the device to change the light conditions to cause the device to react.

FIG. 2 is a side elevational view of the signalling device, with the utensil placed over the photocell of the unit, which utensil is placed at the specified place and location of the photocell to cause the photocell to react and thereby cause the device to react.

FIG. 3 is a schematic circuit diagram of the signalling device.

DESCRIPTION OF THE EMBODIMENT

Briefly stated, the invention comprises a signalling device for providing a person a reminder to regulate the rate or pace of the eating habits of the person at a certain speed to prevent the person from over-eating by eating too fast. The device has a photocell at a specified location on the device having an opening in the device allowing light to reach the photocell. The device adjacent the opening will readily recieve a utensil so as to block out the light in the room to the photo cell to thereby cause the photocell to react to the loss of light with its reaction causing the device to react. The operator, after removing the utensil from the location, presumably to take a bite of food, must replace the utensil within a specified time, timed by the device, or the device will sound an alarm. The operator, further, once he has placed the utensil over the photocell of the device to cause the photocell to react, must leave the utensil over the photocell for a specified period of time, timed by the device, before removing it again to take presumably another bite or a second timing apparatus triggered by an early removal will also sound an alarm, thereby indicating to the operator he or she has removed the utensil too soon, as programed by the device.

Referring more particularly to the drawing, in FIGS. 1 and 2 the signalling device 20 is illustrated having a top 21', bottom 21'' with four sides 21''' forming a box 22. The box has an opening 22' in its top surface 21'. A photo cell 23 is mounted in the box directly beneath the opening, so than an object such as utensil 24 can be placed over the opening in the box to block with its presence, the light in the location where the box is situated to thereby cause the photo cell to react. As shown in FIG. 3, the device 20 has a main switch 25, a first switch or gate 25', a 20 second timer 26 a 15 second timer 27, an 18 minute timer 28, a 2 minute timer 29, an alarm 30, a green indicator light 35'', a red indicator light 32, switches or gates 33, 33', and 33'', timers 34, 34', and gate 35 and various other conventional supporting components such as, resistors, capacitors, and diodes for the operation of the device. The main switch 25 turns on the device 20. The internal control first switch or gate 25', after the activation of the device by turning on the main switch, controls the activation of the twenty and fifteen (15) second timers, and the switch 25'is, in turn controlled by the photo cell 23; while the main switch 25 directly controls the 18 and 2 minutes timers.

The four sides 21''' of the box are relatively narrow or low in height so that the utensil 24 may be placed by the handle 24' over the opening 22' to block the light in the location where the box is situated to cause the photo cell to react, while the rest of the utensil may rest upon the supporting surface 40' that the box rests upon.

The main switch 25 has a hand operated portion projecting out a slot in the top surface 21' for conventionally and manually operating the main switch 25 from outside the box. The device is powered by a D.C. battery 41.

The utensil 24 represents any eating utensil being used. The operator will use the device by turning on the main switch 25 and placing any utensil 24, being used for eating, down over the photo cell 23 after each bite of food in the position illustrated, so that a portion of the utensil blocks the light in the room from coming into the opening 22' to thereby cause the photo cell to react and thereby cause a reaction in the circuit.

When the operator turns on the main switch 25, the power goes to all circuits instantaneously and the device starts to function. The turning on of the main switch automatically activates the 18 minute timer, as part of the 20 (twenty) minutes allowed for the meal by the device. The turning on of the main switch begins the activation of the 18 minute timer by causing the gradual charging of C7 through R18 and R7, which timing charge determines the timing period. This should be approximately 18 minutes. During this timing period, the output of gate 28 (pin 12) will be at a logic state of zero. This output will insure that 1. red indicator light (DS) 32 is off and 2. switch 29 (2 minute) timer will not start timing.

The turning on of the main switch will also cause the dual Flip-Flop 34 and 34' switch to be set to its normal state by causing the charging of C45 through resistor 44. This charging of C45 acts as a clock pulse to switch 34 pin 3 and will cause the following 1. the output pin 1 of switch 34 will be set to a logic state of one (high output voltage) which activates the green indicator light, and 2. the high voltage on pin 1 of switch 34 will also be felt through CR5 to pin 10 of switch 34' to set switch 34' pin 13 to a logic state of zero keeping the alarm from sounding for 15 seconds of the utensil is not over the photo cell and keeps it from sounding until 20 minutes have elapsed if the utensil is over the photo cell and continues to remain there.

An initial turn on of the main switch, if the utensil is not over the photo cell when turned on, one might conclude would sound the alarm through the 20 second timer since 20 seconds has not elasped for the timer to be charged so a utensil could be removed. However, on the initial turn on chip 34 prevents the 20 second timer from turning on the alarm by C45 charging practically instantaneously with turning on the switch and the charging of C45 keeps the alarm from sounding through the 20 second timer. After that time, however, if the utensil is removed and replaced, if the utensil is removed again before 20 seconds have elasped, the chip 34 does not prevent the 20 second timer from activating the alarm.

Assuming the utensil is not placed over the photo cell when the power switch was turned on, the inputs, pin 1 and 2 of gate 25' (the 2 input NAND Gate) will be caused to be set at a logic state of zero. The output pin 3 of switch 25' will as a result be set at a logic state of one. This output will causing the following: 1. timer 27, the 15 second timer, will start timing. If the operator has not placed the utensil over the photo cell by the end of the 15 second timing period, (determined by the charging of C42 through R42) the output pin 12 of switch 27 will go to a logic state of one. This high voltage will be felt through CR46 to the input pins 12 and 13 of gate 40, causing the alarm to sound. If the utensil is placed over the photo cell before the end of 15 seconds, the charging of C42 will be stopped and the alarm will not sound. 2. The output of gate 25' pin 3 will also cause the output of gate 33 pin 11 to be at a zero state and keep timer 26, the 20 second timer from starting.

The placing of the utensil down over the photo cell prevents any alarm from sounding except at the end of the 20 minute period allowed for eating.

If the utensil is on the photo cell when the power switch is turned on, the input pins 1 and 2 of gate 25' will be at a logic state of one, and cause the output pin 3 to be at a logic state of zero. This output will be felt at timer switch 27 through CR42 and will prevent the 15 second timer 27 from starting. The 20 second timer 26 will start timing. At the end of 20 seconds, the output pin 12 of timer 26 will go to a logic state of one and will attempt to set flip flop 34 pin 1 to its normal state. Note: When this has already been accomplished by the charging of C45 through 44 when the power switch was first turned on, the device will stay in a ready condition with the green light on. This is considered the normal starting condition and can be obtained by either 1. Turning the power switch on with the utensil in place or 2. placing the utensil over the photo cell just after turning the power switch on and before 15 seconds have elasped, as either prevents any alarm from thereafter starting and turns off any alarm in progress.

OPERATION

Assuming the operator has turned the main switch on with the utensil in place over the photo cell, the next step would be for the operator to remove the utensil from the photo cell to take a bite of food. The operator does not have to wait the 20 second elapse since the turning on of the main switch, this first time, as the green light is on as though the 20 seconds have already elasped. This removal will cause the 15 second timer 27 to start timing, while the green light remains on. The operator has 15 seconds to take a bite of food and replace the utensil over the photo cell or the alarm will sound.

If the 15 second period is exceeded, the alarm will sound, however, placing the utensil over the photo cell will stop the alarm by causing the output pin 3 of gate 25' to go to a logic state of zero, which sets timer 27 pin 12 to its normal state of zero by C42 discharging to zero. This in turn is felt on pins 12 and 13 of gate 40 through CR46 and will stop or detactivate the alarm.

Placing the utensil on the photo cell either before the 15 second timing period has elasped or after will cause the output of switch 25, pin 3 to go to a logic state of zero and will start the 20 second timer 26. This is done by the output of gate 33, pin 11 going to a logic state of one. This high voltage will cause several things to take place. 1. C43 will start charging through R43 and will determine the 20 second timing period. 2. The zero-voltage to high-voltage transition on gate 33 pin 11 will be felt on flip flop 34 pin 4 through C44 and will cause switch 34 to be reset. The output pin 1 of switch 34 will go to zero and cause the following: 1. The green ready light 35" will go out. 2. The zero voltage on switch 34 pin 1 will be felt on gate 33" pins 5 and 6 and cause switch 33' pin 4 to go to a logic state of one and will cause the one shot circuit of gates 33, 33', and 33" pins 8 through 13 to be set in a locked condition. This locked condition will reject any further information received on gate 33 pin 12, from interfering with the 20 second timing period. This condition will continue until the 20 second timing is complete and flip flop 34 is set to its normal state, turning on the green light 35". 3. The output pin 2 of flip flop 34 will go to a high voltage and will be felt on switch 34' pin 9. The output pin 13 of flip flop 34' will now react to any removal of the utensil.

If the utensil, before the 20 seconds has elasped, is removed the alarm will sound caused by the output of gate 25' pin 3 going from a zero voltage to a high voltage, causing C47 to charge through R47 and work as a clock pulse to flip flop 34' pin 11. This clock pulse will cause switch 34' pin 13 to go to a logic state of one and cause the alarm to sound.

If the utensil is again replaced, before the 20 seconds has elasped over the photo cell, the output of switch 25' pin 3 will go to zero state and will be felt at the input of gate 35' pins 1 and 2. This will cause the output pin 3 of gate 35' go high and will be felt on pin 10 of flip flop 34' through CR47. This will cause the output pin 13 of switch 34' to be reset to a zero voltage and will stop the alarm.

The above sequence will be repeated each time the utensil is removed or replace during the 20 second period.

When the 20 second timing period is complete, flip flop 34 be set to its normal state by timer 26 pin 12 going to a high voltage. The ready indicator light (green) 3511 will turn on. The system is now ready for the operator to remove the utensil and take another bite without sounding the alarm.

The sequence of removing the utensil, taking a bite, replacing the utensil within 15 seconds, then waiting 20 seconds before removing it to take another bite can be repeated for approximately 18 minutes. At this time, the 18 minute timer, starting when the main switch was turned on, will cause timer 28 pin 12 to go to a high voltage. This high voltage will cause 1. the 2 minute red indicator light 32 to light up, and 2. allow C48 to start charging, starting the 2 minute timer 29.

The red indicator light 32 indicates to the operator he has only two minutes left of the 20 minute timing limit set by the device for the entire meal.

At the end of the two minute timing period, the output pin 12 of timer 29 will go high. This high voltage will be felt at switch 40 pins 12 and 13 through CR 49 and will cause the alarm 30 to sound. The alarm 30 will sound until the main switch 25 is turned off.

Thus, briefly, the operation allows the operator 15 seconds to take a bite by removing the utensil and if he replaces the utensil within that time the alarm will not sound, and it requires the operator to delay at least 20 seconds after taking a bite and replacing the utensil before he can remove the utensil to take another bite, and if the operator follows this sequence, the device will not sound the alarm until the end of the 20 minute period allowed for the entire meal.

The green light will come on when 20 seconds has elasped since replacing the utensil and the red indicator light will come on when 18 minutes has elasped since turning the device on.

The device, by allowing the operator to use the utensil for 15 seconds for taking a bite, assuming only one bite for each fifteen seconds, and by causing him or reminding him by the alarm to leave his utensil down for 20 seconds between each bite, thereby acts to regulate the rate of eating of the operator by regulating the number of bites he or she takes at timed intervals Thus, it will be seen that a novel timing device has been provided to regulate the eating habits of a person to prevent his or her overeating. Different specific times for the switches could be utilized.

The timers 26, 27, 28, and 29 are of a conventional type wherein the length of time it takes for each timer from activation, by allowing their capacitors to receive sufficient current through their resistors R43, R42, R18 and R7, and 31, respectively, until their capcitors are sufficiently charged to trigger or change the values of their output pins, such as pin 12, to positive as determined primarly by the values of the resistors for each timer. The higher value resistors cause the current to take longer to travel through and charge up the capacitor, consequently, the timers with the longer clocking timer before triggering having correspondingly higher value resistors than timers with shorter clocking time before triggering. Thus, timer 28 has the highest clocking time of 18 minutes and it correspondingly has the highest value resistors and the other timers have correspondinng resistors with lower values. The capacitors also have values cooperating to that result.

In place of a photo cell 23, a mechanical switch may be utilized to be activated by the engagement with the utensil to change the condition of the voltage in gate 33. The timers employed in the device are conventional chip timers, and the switches and other components are of a conventional type. In addition, dim-bright switches may be provided to vary the intensity of the various light indicators in the device, should the photo cell switch be used.

The device assists people in reminding them to eat slowly and after repeated use to change their eating habits to eat more slowly.

It will be obvious that various changes and departures may be made to the invention without departing from the spirit and scope thereof, and accordingly, it is not intended that the invention be limited to that specifically described in the specification or as illustrated in the drawing, but only as set forth in the appended claims wherein

What is claimed is:

1. A signalling device for reminding persons to follow certain eating habits when eating a meal comprising a main switch, a photo cell, an alarm, timers to divide the eating of a meal in accordance with time frame as predetermined by said timers and to sound said alarm when the operator does not follow the time frame, said photo cell being reactive to the placement or removal of a utensil thereover, said timers including one timer to time the time required by a person between each bite of a meal and to sound said alarm when the operator does not delay the predetermined time required by the program of the device between each bite of a meal, said timers further including a timer to time the required amount of time for taking each bite of a meal and to sound said alarm when the operator takes more than the predetermined amount of time allowed by the switch for taking a bite of a meal, said first mentioned timer being activated by said photo cell upon placement of the utensil and responding to the removal of the utensil from the photo cell to sound the alarm if the utensil is removed too soon after its placement, said second mentioned timer being activated by said photo cell upon removal of the utensil from the photo cell to start timing the time allowed by said timer for taking a bite and to sound said alarm if the operator takes too long to replace the utensil over the photo cell.

2. A signalling device according to Claim 1 wherein said timers include a third timer activated by said main switch and actuating signalling means after a relatively long period of time in relation to the first and second mentioned timers to signal that the meal is nearly over, and a fourth timer activated by said main switch to activate an alarm after a period of time slightly longer than the activation of the third timer to indicate to the operator the meal is considered over.

3. A signalling device comprising triggering means, alarm means, a plurality of timing means, switching means, said device having a structure adapted to enable a utensil to be used in conjunction with said device by said structure's enabling and facilitating a utensil to be placed into operative engagement with said triggering means to activate said triggering means, said timing means acting to sound said alarm at certain timed intervals in conjunction with the placement of said utensil into operative engagement with said triggering means to indicate to a person, if that person places said utensil into operative engagement with said triggering means after each bite, when he is eating too fast by taking too many bites in an interval of time with said utensil in the estimation of the device, said timing means including a first timing means that sounds an alarm if the operator does not replace the utensil into operative engagement with the triggering means within a specified period of time, said timing means including a second timing means that will sound an alarm if the operator removes the utensil from operative engagement with the triggering means in less than a specified period of time programmed by the device after having replaced the utensil into operative engagement with the triggering means to thereby regulate the number of bites taken with said utensil to an acceptable rate.

4. A signalling device for reminding persons to follow certain eating habits when eating a meal comprising a series of timers to time the entire divide of eating a meal in accordance with timed routine predetermined by the timer and an alarm to sound when the operator does not follow the timed routine to thereby cause the operator to follow the timed routine preprogramed into the device, said timers including a first timer to time the entire time programmed as adequate for a complete meal from beginning to end and to sound said alarm when the end of the meal has been reached as programmed by the device, said timers including a second timer to time the time required by a person between each bite of a meal and to sound said alarm when the operator does not delay the predetermined time required by the program of the device between each bite of a meal, said timers including a third timer to time the required amount of time for taking each bite of a meal and to sound said alarm when the operator takes more than the predetermined time alloted by the program of the device for taking a bite of a meal, a main switch, a photo cell reactive to the placement or removal of a utensil therefrom, said first timer being activated by said main switch, said second timer being activated by said photo cell upon placement of the utensil over the photo cell, presumably after taking a bite of a meal, and to sound said alarm if the utensil is removed again too soon after its placement, presumably to take another bite of the meal, said third timer being activated upon removal of the utensil from the photo cell to start timing the time allowed by said timer for taking a bite and to sound said alarm when the operator takes too long to replace the utensil.

* * * * *